US006537575B1

(12) United States Patent
Firestone et al.

(10) Patent No.: US 6,537,575 B1
(45) Date of Patent: Mar. 25, 2003

(54) SYNTHETIC BIOLOGICAL MEMBRANE WITH SELF ORGANIZING PROPERTIES

(75) Inventors: Millicent A. Firestone; David M. Tiede, both of Elmhurst, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/627,808

(22) Filed: Jul. 28, 2000

Related U.S. Application Data

(60) Provisional application No. 60/146,610, filed on Jul. 30, 1999.

(51) Int. Cl.[7] .................... A61K 9/14; A61K 31/74; A61K 9/127; A61K 47/30
(52) U.S. Cl. ................ 424/484; 424/78.17; 424/489; 424/450; 514/772.1
(58) Field of Search ................ 424/484, 450, 424/489, 78.17, 772.1; 514/781

(56) References Cited

U.S. PATENT DOCUMENTS 5,492,937 A  *  2/1996  Bogentoft et al. .......... 514/781

OTHER PUBLICATIONS

Firestone et al., "Structure and Optical Properties of a Thermoresponsive Polymer–Grafted, Lipid Based Complex Fluid" Langmuir, vol. 14, No. 17, p 5688–4698.*

Firestone, Millicent, et al., Magnetic Field–Induced Ordering of a Polymer–Grafted Biomembrane—Mimetic Hydrogel, The Journal of Physical Chemistry, Mar. 23, 2000, pp. 2433–2438, vol. 104, No. 11, American Chemical Society, U.S.

Firestone, Millicent, et al., Structure and Optical Properties of a Thermoresponsive Polymer–Grafted, Lipid Based Complex Fluid Langmuir, vol. 14, No. 17, pp. 4688–4698.

* cited by examiner

Primary Examiner—Thurman K. Page
Assistant Examiner—Blessing Fubara
(74) Attorney, Agent, or Firm—Cherskov & Flaynik

(57) ABSTRACT

A mixture is provided which manifests a gel phase at a temperature higher than that in which the mixture manifests a liquid phase. The mixture is a combination of a lipid, a polymer-grafted phospholipid and a surfactant. It is biomimetic in nature and changes phases when subjected to one or a plurality of environmental stimuli.

23 Claims, 4 Drawing Sheets

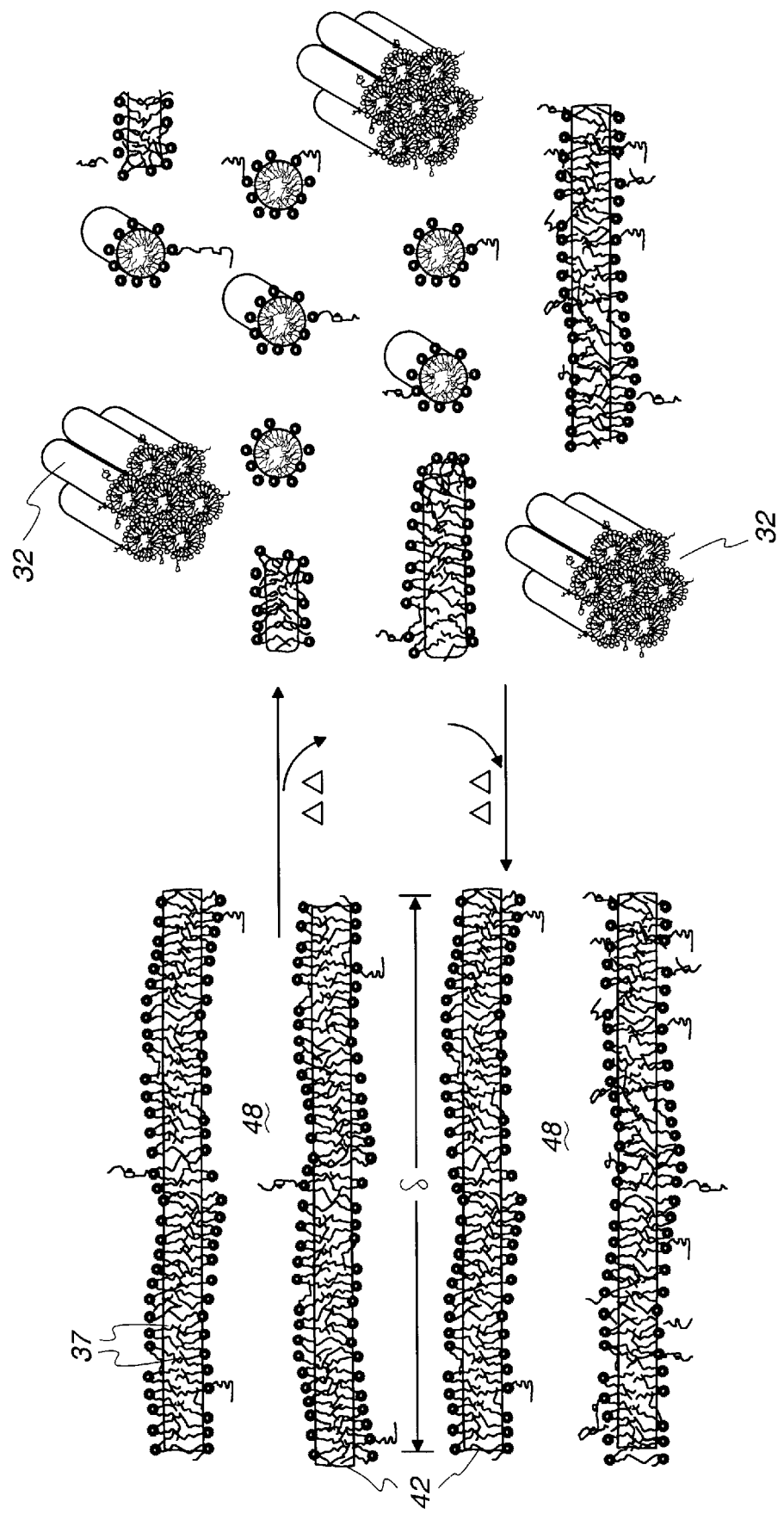

SYNTHETIC BIOLOGICAL MEMBRANE WITH SELF ORGANIZING PROPERTIES

This application is related to Provisional Patent Application No. 60/146,610, filed Jul. 30, 1999

CONTRACTUAL ORIGIN OF THE INVENTION

The United States Government has rights in this invention under Contract No. W-31-109-ENG-38 between the U.S. Department of Energy and the University of Chicago representing Argonne National Laboratory.

BACKGROUND OF THE INVENTION

1. Field of the Invention

The present invention relates to synthetic biological membranes with self organizing characteristics, and more particularly, the invention relates to membrane-mimetic liquid crystalline gels which change shape and function as a response to environmental changes.

2. Background of the Invention

In recent years, there has been increasing interest in the development of so-called "intelligent" or "smart" materials whose properties change in response to such environmental conditions as ionic strength, temperature, and magnetic- or electric-fields. The ability to control the structure and therefore the function of materials by application of external stimuli forms the basis of molecular machines, chemical valves and switches, sensors, and a wide range of optoelectronic materials.

Considerable effort is being expended to develop smart materials which can serve as vehicles to transport biological and non-biological materials. One such material is composed of a mixture of lipids, a low molecular weight polyethylene glycol-derived polymer lipid, and a pentanol surfactant. Warrnier, H. E. et al *Science*, (1996), 271, pp969–973. These gels change to a liquid by heating to a higher temperature. However, both the pentanol surfactant and elevated temperatures cause rapid degeneration of incorporated proteins and other biomolecules in the materials. Also, the material appears to undergo phase separation at reduced temperature. Lastly, the material does not seem to react to external stimuli other than temperature variations.

A need exists in the art for a material that is responsive to a variety of environmental stimuli. The material should be capable of transporting and/or spatially organizing biological components. The material should be comprised of matter, and exhibit physicochemical properties (e.g. phase changes) that are compatible to the biological material or to the target for the biological material. And the material should exhibit phase changes which are reversible.

SUMMARY OF THE INVENTION

It is the object of the present invention to provide a smart gel which over comes many of the disadvantages of the prior art.

Another object of the present invention is to provide a fluid which undergoes macroscopically observable structural and functional changes in response to an environmental stimulus, or to a myriad of environmental stimuli. A feature of the invention is its existence as a gel at relatively high temperatures, and its existence as a liquid at low temperatures. An advantage of the invention is its use as a drug delivery system wherein the high temperature point of the system is the body temperature of a target organism or target structure.

Another object of the present invention is to provide a biocompatible, membrane-mimetic liquid-crystalline material. A feature of this invention is the ability to package or encapsulate biologically active membrane proteins, membrane-associated biomolecules within an organized lipid matrix. An advantage of the invention is its use to encapsulate and spatially organize proteins, biomolecules, organics, and inorganic material while simultaneously protecting these encapsulated entities from degradation. This capability allows the invented mixture to produce and/or deliver membrane bound molecules or associated molecules, protected in the matrix, in their biologically or functionally active states in drug delivery applications, and in organized lipid-based arrays for device and assay applications.

Still another object of the present invention is to provide a mixture which provides functional characteristics in response to certain environmental stimuli, when certain structural characteristics are induced by other environmental stimuli. A feature of the invention is that macroscopic ordering of molecules occurs when a magnetic field, an electric field, or shear is applied to the mixture, but only when the mixture is at a certain temperature. An advantage of the invention is that such synergy between stimuli renders the mixture as a multi-positional or multi-variable switch.

Yet another object of the present invention is to provide a mixture which reacts to external stimuli to provide both structural and functional characteristics. A feature of the invention is that it manifests a birefringent phase when subjected to a certain environment, an optically isotropic (nonbirefringent) or transparent phase when subjected to another environment, and the ability to display visual confirmation of intact membrane structure associated with the birefringent phase. An advantage of the invention is an optical cue that an intact membrane has formed in response to application of certain stimuli.

Briefly, the invention provides for a material which undergoes a thermoreversible phase change, the material comprising a mixture of a lipid, a polymer amphiphile (such as a polymer-grafted phospholipid), a co-surfactant, and water.

Also provided is a method for delivering, encapsulating and/or transporting medicaments to a patient, the method comprising combining the medicaments with a liquid phase solution at a predetermined temperature to create a liquid mixture; increasing the temperature of the mixture to a second predetermined temperature so as to cause the mixture to solidify; and administering the solidified mixture to the patient.

The invention also provides a material which undergoes a thermoreversible phase change, the material comprising 65 to 90 percent by weight of water, 3 to 5 weight percent of surfactant, 7 to 27 weight percent lipid plus amphiphilic polymer, wherein the amount of polymer to lipid is approximately 4 to 10 mole percent.

BRIEF DESCRIPTION OF THE DRAWINGS

These and other objects and advantages of the present invention will become readily apparent upon consideration of the following detailed description and attached drawings, wherein:

FIG. 4 is a schematic depiction of the mixture undergoing phase change; and

DETAILED DESCRIPTION OF THE INVENTION

A self assembling, stimulus-responsive fluid has been invented that switches between two distinct structural states and two distinct functional states in response to a myriad of environmental stimuli. The material is formed by the non-covalent self-assembly of a quaternary mixture of a phospholipid, a lipopolymer, or diblock or triblock co-polymer or polymer-grafted amphiphile, and a surfactant dispersed in water. The result is a non-denaturing artificial membrane matrix suitable to incorporate and encapsulate desirable reaction centers such as biological molecules (e.g. proteins and enzymes). More explicit detail on the material and methods for preparation of the invented fluid is found in Firestone et al, *Langmuir* 1998, 14, 4688–4698, and incorporated herein by reference.

The resulting supra molecular assembly undergoes a reversible transformation from a liquid-crystalline gel to a nonbirefringent fluid upon reduction in temperature. Conversely, the liquid phase is found to spontaneously organize into a liquid crystalline gel with an increase in temperature. These changes occur at the molecular level but manifest themselves as a macroscopically observable phase and structural changes. These thermoreversible phase changes occur at temperatures of between approximately 15° C. and 20° C. Similar structural changes are induced by other environmental stimuli, such as exposure to a magnetic field, an electrical field, and/or shear forces.

Figure 1:
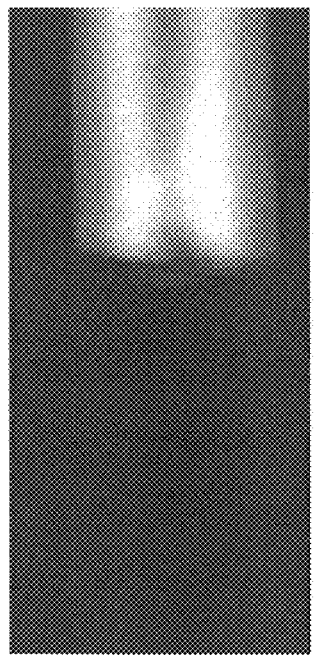
FIG. 1A is a photomicrograph of an exemplary material displaying birefringence, in accordance with features of the present invention.
FIG. 1B is a photomicrograph of the exemplary material displaying a lack of birefringence when its temperature is lowered, in accordance with features of the present invention.
Figure 2:
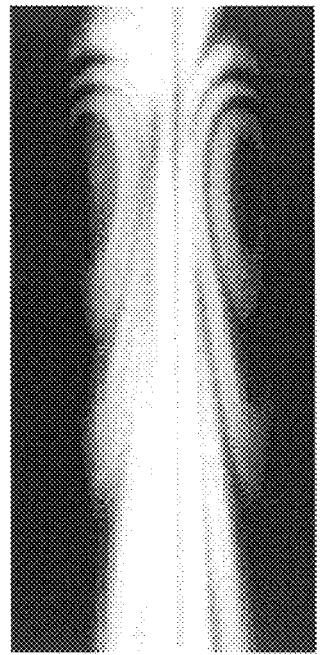
FIG. 2 is a photomicrograph of the material depicted in FIG. 1A but subjected to an external magnetic field, in accordance with features of the present invention.

FIG. 1 and FIG. 2 illustrate the properties of the invented material using polarized light microscopy. The micro structure was easily determined with this technique inasmuch as the intensity of light transmitted through the material placed between crossed polarizers is related to the material's anisotropy.

FIG. 1A depicts the gel phase (room temperature phase) whereby liquid crystalline textures, characteristic of an anisotropic medium, are visible. In this instance, the gel was placed in a 5 mm NMR tube at 25° C. Room temperature measurements using small angle neutron and x-ray scattering techniques indicate that the aggregated morphology at room temperature is multilamellar, as evidenced by three and five orders of diffraction, respectively.

When a lower portion of the material is contacted with ice (FIG. 1B), a sharp boundary between the upper birefringent gel phase and the lower non-birefringent liquid phase becomes evident.

FIG. 2 illustrates that persistent structural changes and enhanced asymmetry are induced in the gel by exposure to a magnetic field. In this instance the material is exposed to a 7.2 tesla (T) magnetic field for 25 minutes and then warmed through the phase transition to the gel phase. Again using polarized light microscopy, significant changes in the optical birefringence (i.e. liquid crystalline textures) of the material was observed with increasing exposure to a magnetic field. The observed brilliant polarization colors are formed as a result of interference (either partial or complete) as white light passes through the material. Furthermore, the polarization colors intensify and their patterns increase in complexity (i.e. grow sequentially) with increasing magnetic field strength and/or exposure time.

The increasing intensity and complexity of the pattern with magnetic field exposure indicates that the gel phase material can be transformed from a typical liquid crystalline phase material with molecules oriented in small domains or regions to a macroscopically aligned gel with cooperative alignment or orientation of the domains. The inventors have found that the highest order of polarization color (i.e., the optical path length difference) exceeds third order after magnetic field exposure. As such, the potential of growing very large ordered domains (regions of aligned molecules) in the presence of a magnetic field has been realized.

The invented mixture is unique in providing structural and functional changes which are counter-intuitive to those skilled in the art. For example, the material's thermoreversible phase change characteristic can be utilized as a chemical valve, chemical actuator, or some other type of physico-chemical switch. An analogous application is as a drug delivery system wherein the fluid coalesces at body temperature so as to provide slow release of medicaments previously mixed with the fluid during cold processing.

Inasmuch as the invented material, upon coalescence, mimics cell membrane structure, the utilization of the material in gene therapy, as artificial tissue, or as another vehicle for drug delivery, is suitable. Given the colloidal nature of such membranes, wherein polar groups extend outwardly in physiologic situations, the encapsulation of proteins, organic molecules, aqueous molecules, metals and colloidal metals (such as semiconductor colloids) is facilitated with the invented material. Its use as a vehicle for infectious vectors also is evident. Suitable metals are gold, silver, cadmium sulfide, and various semiconductors. Suitable size ranges of the metals and semiconductor colloids are from 2 to 20 nanometers (nm).

The phase change aspects of the invented material also can be utilized in spin coating/solvent casting operations.

The birefringent variations of the material, wherein the material is optically isotropic at one environmental condition and then optically birefringent at another environmental condition, makes the material particularly suitable as an optical information storage and processing media. In instances where magnetic field effects alter the birefringent nature of the material, magnetic information storage applications also are facilitated.

With the invented fluid also affected by applied electric fields, its application in nonchemical lithography processes is suitable.

When in a relatively high temperature environment, the invented mixture is a multilamellar liquid-crystalline gel comprising alternate sheets of water and lipid bilayers incorporating the co-surfactant. Below the phase transition temperature, the mixture is a non-birefringement liquid, i.e., optically isotropic. Also below this temperature, the macroscopic ordering noted above with H-field application is erased. As such, this magnetic effect can be used to orient encapsulated proteins and molecules.

Figure 3:
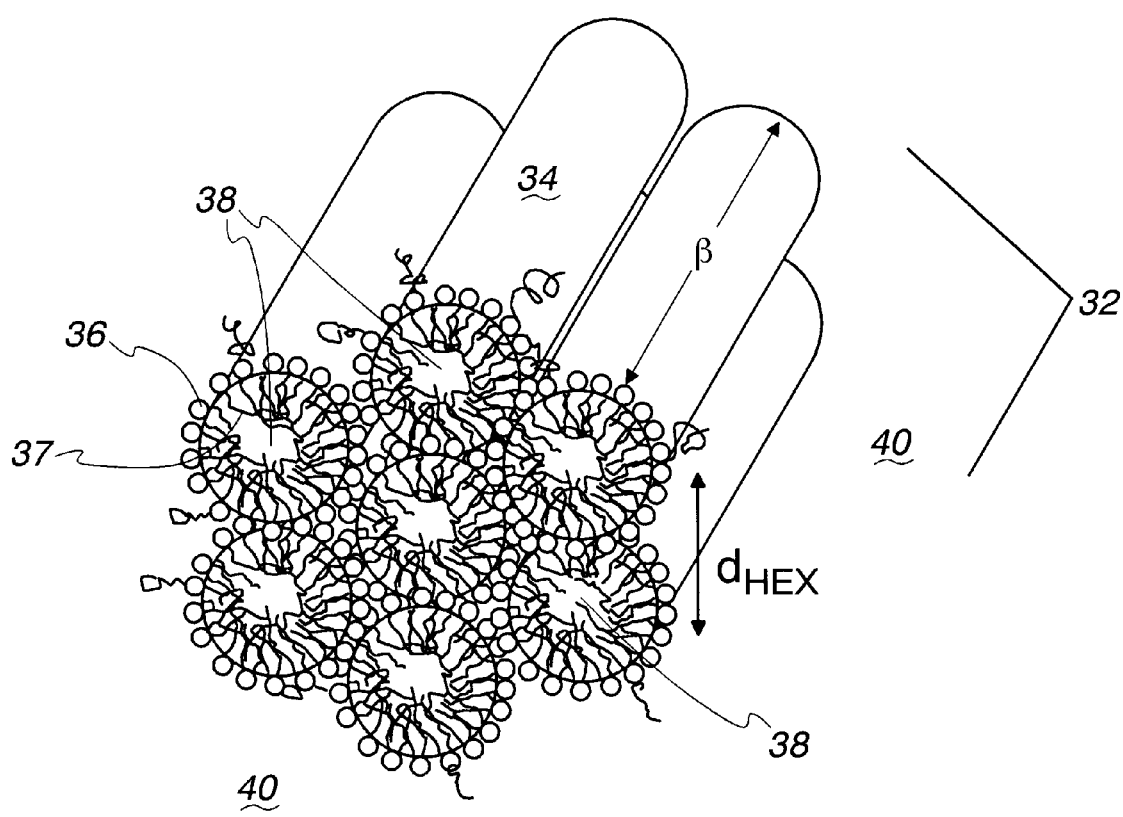
FIG. 3 is a schematic depiction of the invented mixture in liquid phase.

As depicted in FIG. 3, the liquid phase of the invented material has a structure analogous to a micro-scaled, two-dimensional array 32 of cylinders 34. One such structure has a lattice spacing $d_{hex}$ (i.e., the distance between the center of adjacent cylinders or tubes) of several hundred angstroms. The topology of the liquid phase is a normal hexagonal structure in which the hydrocarbon chains 37 of lipids 36 fill the interior 38 of the cylinders 34, and the cylinders are immersed in a water continuum 40.

The absence of birefringence in the liquid phase depicted in FIG. 3 is believed to arise from the shortened axis β of the cylinders compared to its counterpart δ seen in the liquid crystal phase, so depicted in FIG. 4A.

The gel composition illustrated in FIG. 4A, may be characterized as a mixture of a phospholipid, a polymer amphiphile such as an end-grafted phospholipid or a diblock copolymer or a triblock copolymer, and a zwitterionic or cationic co-surfactant dispersed in water. These gels form bilayer membranes 42 with the hydrophobic ends 37 of the lipid and co-surfactant of each layer oriented inwardly. Intermediate these membranes are cavities or spaces 48 which can accommodate whatever fluid in which the membranes are immersed. The juxtaposition of the membranes 42 relative to each other results in the cavities or spaces 48 being differentially organized into planar sheets and channels separated by the water impermeable lipid micelle and membranes 42.

Generally, the ratios of the components of the invented quanternary mixture can vary as follows: 0.65–0.9 weight percent of water, 0.03 to 0.05 weight percent of cosurfactant, 0.07–0.27 weight percent of total lipid (which includes lipid plus amphiphilic polymer), and within the total lipid, 4–10 mol % of amphiphilic polymer.

Proteins or other moieties, generally of a size of between 1 nm and 50 nm, may be incorporated in the bilayer membranes or in the aqueous channels 48. This would allow the membrane to be used as a package or to encapsulate samples of proteins and other organics for analysis and for carrying medications into the blood stream for slow release. Characteristics of the gels could also be the basis for use in sensors and opto- and micro-electronic products.

The inventors have found that the mesoscopic (i.e., nanometer to micrometer-scale) self assemblage of the invented fluid is further enhanced when the fluid contacts an appropriate surface. For example, when the gel-phase of the mixture communicates with certain surfaces containing hydroxyl moieties (such as glass), orientation of the lamellar domains of the gel are directed into macroscopic dimensions. This ordering enhancement is due to an interaction between the polar phospholipid head groups contained in the mixture and a similar hydrophilic group on the support substrate. This phenomenon makes the mixture particularly suitable for holding target moieties encapsulated by the mixture in a certain orientation for further analysis.

This enhancement of,ordering is particularly valuable when utilizing the fluid to form membranes in association with, or immobilization to, desired solid surfaces, or other substrates having functional moieties which interact with a functional group contained in the fluid.

Magnetic Field
Application Detail

Figure 5A:
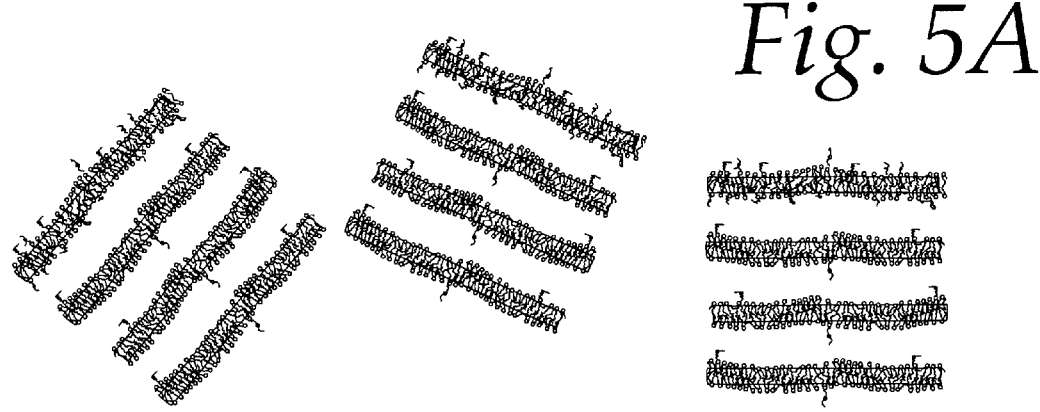
FIGS. 5A–5C are schematic depictions on the invented lamella in the absence of magnetic fields, and in the presence of magnetic fields before and after the introduction of paramagnetic reagents, in accordance with features of the present invention.
Figure 5B:
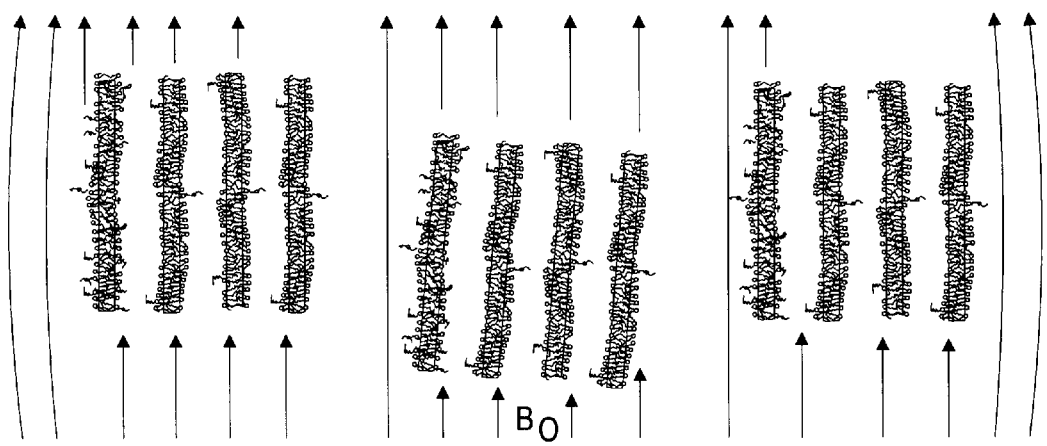
Figure 5C:
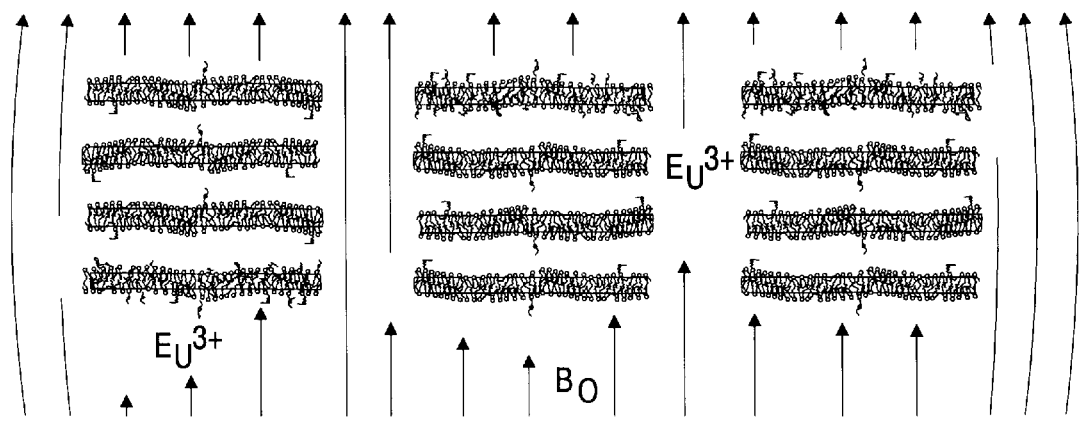

As noted supra, the structure,size and characteristics of the lamellar structure are affected by temperature, shear field phases of the aqueous lipid, surfactant mixture, and polymer amphiphile utilized. These:characteristics are further effected with the imposition of magnetic fields, as depicted in FIGS. 5A–5C. Specifically, without the application of a magnetic field, lamella appear in a jumbled state, as illustrated in FIG. 5A.

However, the inventors have found that a rapid persistent macroscopic alignment of lamella occurs when a magnetic field (See FIG. 5B). As noted in Firestone et al. *J. Phys. Chem. B*, 104, No. 11, pp 2433–2438, and incorporated herein by reference, the axis of the lamellar domains orient perpendicularly to the applied H-field. (It should be noted here that the axis of lamellar domains is the axis of the repeat units, called the Director.) This perpendicular orientation persists even after field termination. This high degree of persistent anisotropy is achievable due to the inverted, thermoreversible phase transition characteristic of the invented fluid.

Furthermore, as depicted in FIG. 5C, the inventors found that the lamellar domains can be manipulated to orient parallel to the H-field when paramagnetic reagents, such as Lanthanide ion are incorporated into the invented material. The resulting parallel juxtaposition of the lamella to the H-field facilitates orientation of molecules (e.g., α-helical proteins) having large positive magnetic susceptibilities which would otherwise cancel or limit attainable bicelle alignment. The paramagnetic reagents are added to the buffer component of the composition prior to H-field application. Suitable reagents include, but are not limited to, lanthanide ions, paramagnetic shift reagents, and magnetic nanoparticles.

The application of the magnetic field in essence facilitates the ordering of the lamellar domains and therefore eliminates unfavorable orientations and defects associated with this material which may otherwise be effected with unchecked Brownian motion. In fact, the inventors have found that the anisotropic alignment of the domains is macroscopic in scope.

Surprisingly and unexpectedly, the success of magnetic field application in generating ordered lamellar domains is enhanced when dealing with materials having phase-transition characteristics of the type exhibited by the invented material. For example, warming the material through the phase transition during H-field application, allows for coalescence of aligned tubular micelles, (a single species of which is depicted in FIG. 3) into extended ordered lamellar domains. This is accompanied by the onset of a highly viscous gel phase that acts to "lock in" the field-induced sample assymmetry.

A myriad of H-field strengths can be utilized to facilitate alignment of the invented material. Suitable field strengths are anything above 0.1 T.

Lipid Detail

The inventors have arrived at several variations on the basic four component (i.e., lipid+polymer+co-surfactant+water) recipe of the invented material. With regard to lipid, the inventors have found that increasing the acyl chain length from approximately 12 carbons to 22 carbons results in increasing the phase transition temperature. As such, drug delivery vehicles can be produced with the gel-to-fluid phase transformation to occur at body temperature.

Suitable lipids include a phosphatidylcholine (PC) having from 14 carbon atoms, such as dimyristolyphosphatidylcholine (DMPC), to one having 18 carbon atoms, such as distearoylphosphatidylcholine (DSPC). Generally, lipids having from 12 to 22 carbons are suitable.

Polymer Detail

Amphiphilic polymer is utilized in the mixture as the means for tuning the structure and properties of the material. Several different types of polymers are suitable components for the invented mixture. One type are the polyethylene glycolated phospholipids. Exemplary species of these "pegylated" phospholipids include 1,2-dimyristoyl-snglycero-3-phosphoethanolamine-N-[poly(ethylene gylcol)], (DMPE-E)(45)2000) and 1,2-dimyristoyl-sn-glycero-3-phosphoethanolamine-N-[poly(ethylene glycol)] (DMPE-EO(99)5000). With regard to DMPE-EO(45)2000, 45 designates the number of repeat units of the ethylene glycol, with 2000 indicating the molecular weight. With these types of polymers, inclusion is via covalent attachment to the lipid, as detailed in the Langmuir paper earlier incorporated by reference.

However, an alternative approach that yields similar phase properties involves the introduction of triblock polymers such as $EO_x$-$PO_y$-$EO_x$, available from ICI Surfactants of New Castle, Del. One such triblock polymer is $EO_{99}$-$PO_{85}$-$EO_{99}$.

Another approach is the addition of polyoxyethylene esters such as those available from SIGMA/ALDRICH of St. Louis, Mo.

Non-EO-based materials, such as oligomers of N-isopropylacrylamide also are polymer choices. The inclusion of such macromolecules include end-grafting the macromolecules onto phospholipids or the synthesis of polymer amphiphiles in which the alkyl chains can function to anchor the amphiphile into the bilayer.

Surfactant Detail

Zwitterionic surfactants confer the desired membrane characteristics of the invented mixture. Exemplary zwitterionic or amphoteric surfactants include lauryldi-methylamine-oxide (LDAO), and N-dodecyl-N,N-dimethylamino butyrate (DDMAB).

Furthermore, cationic surfactants such as cetyltrimethyl-ammonium bromide (CTAB) yields a similar material with some variations in the structure of the cold phase, i.e., the liquid.

EXAMPLE 1

A mixture comprising the phospholipid di- myristoly-phosphatidylcholine (DMPC), a lipopolymer consisting of poly(ethylene oxide) terminally grafted onto the phosphate headgroup of 1,2-dimyristoyl-sn-glycero-3-phosphoethanolamine-N-[poly(ethylene glycol)], (DMPE-EO45, also referred to as DMPE-PEG2000) and the cosurfactant, lauryldi-methylamine-oxide (LDAO) was dispersed in water. The quanternary composition comprised 0.8 weight percent of water, 0.03 weight fraction of co-surfactant, 0.17 lipd, with a PEGylated phospholipid to total lipid content of 8 mol %.

In this mixture, the onset of thermotropic phase transition was between approximately 16° C. and 18° C. as determined by differential scanning calorimetry (DSC). Essentially, the transition was from a non-optically birefringent, two-dimensional normal hexagonal micellar phase to an optically birefringent lamellar phase gel. This transformation is reversible.

The lattice spacing of the liquid phase was approximately 345 Å. Structural characterization by phosphorous 31 nuclear magnetic resonance (31P NMR) and small angle neutron scattering (SANS) demonstrates that the gel phase comprises microdomains of lamella with a lattice spacing of 153 Å. The lamellar structure, however, is a high defect structure, as evidence by polarized optical microscopy (POM) and broad Bragg peaks of the small-angle neutron diffraction profile.

Analysis via transmission Fourier transform infrared (FT-IR) indicates high gauche content, which indicates that gelation is not a consequence of alkyl chain ordering. Rather, the inventors surmise that it is changes in the polymer conformation that gives rise to the structural changes.

The material can be produced by varying the water content between 70 percent and 90 percent, and adjusting the solid components accordingly.

As noted supra, the inventors found that the long range structural ordering of the material can be enhanced by external field processing (e.g., by the application of magnetic or electric fields, or shear). The inventors have determined that a magnetic field of at least 0.1 Tesla imparts desired structural ordering, which in turn leads to enhanced birefringence.

As noted supra, the inventors have found that this ordering can be facilitated or further enhanced with another environmental stimulus, for example, communication of the material with a surface template having functional moieties which interact with mixture components. This interaction serves to direct orientation of various compo nents of the mixture to a predetermined orientation for later utilization in assay scenarios.

A variety of materials have been encapsulated and organized by the invented fluid, including membrane and aqueous soluble proteins, other nanostructrues, such as metal nanoparticles, and both organic and inorganic small molecules. Specific encapsulation moieties include nano-metallic particles, such as gold and silver, azobenzene derivatives, and stilbene-based chromophores, the last of which are second order, nonlinear optical materials which doubles the frequency of light impinging upon them.

While the invention has been described with reference to details of the illustrated embodiment, these details are not intended to limit the scope of the invention as defined in the appended claims.

The embodiment of the invention in which an exclusive property or privilege is claimed is defined as follows:

1. A material which undergoes a thermoreversible phase change, the material comprising a mixture of a lipid, a polymer-grafted phospholipid, a co-surfactant, and water.

2. The material as recited in claim 1 wherein the material changes from a gel phase to a liquid phase upon reduction in temperature.

3. The material as recited in claim 1 wherein the phospholipid contains from 14 to 18 carbon atoms.

4. The material as recited in claim 1 wherein the phospholipid is dimyristolyphosphatidylcholine C-14, or distearolyphosphatidylcholine C-18 or combinations thereof.

5. The material as recited in claim 1 wherein the polymer-grafted phospholipid is a polyethylene glycolated phospholipid.

6. The material as recited in claim 1 wherein the phase change occurs between 15° C. and 20° C.

7. The material as recited in claim 2 wherein the gel phase undergoes a change in birefringence when subjected to a magnetic field.

8. The material as recited in claim 1 wherein the material defines a structure which converts between organized micelles to a biomimetic lamellar membrane upon exposure to an environmental stimulus.

9. The material as recited in claim 8 wherein the magnetic field has a strength of at least 0.1 tesla.

10. The material as recited in claim 9 wherein in one configuration, the material defines a membrane which is adapted to receive selected moieties.

11. The material as recited in claim 9 wherein the moieties are encapsulated so as to form arrays of the moieties.

12. The material as recited in claim 10 wherein the moieties are metal-containing moieties ranging in size from 2 nm to 20 nm.

13. The material as recited in claim 12 wherein the metal-containing moieties are gold, silver, cadmium sulfide, or semiconductor colloids.

14. The material as recited in claim 10 wherein the moieties are medicaments selected from the group consisting of inorganic material, organic material, or combinations thereof.

15. A material which undergoes a thermoreversible phase change, the material comprising between approximately 65 to 90 percent by weight of water, 3 to 5 weight percent of co-surfactant, 7 to 27 weight percent lipid and polymer amphiphile, wherein the amount of polymer amphiphile to lipid is approximately 4 to 10 mole percent.

16. The material as recited in claim 15 wherein the material manifests a liquid phase at a lower temperature than it manifests a solid phase.

17. The material as recited in claim 15, wherein the material comprises 80 percent by weight of water, 3 weight percent of surfactant, 17 weight percent lipid, and an amount of polymer grafted phospholipid to total lipid of approximately 6 mole percent.

18. The material as recited in claim 1 wherein the material is optically isotropic at one environmental condition and optically birefringent at a second environmental condition.

19. A biocompatible membrane-mimetic liquid-crystalline material comprising a lipid, polymer-grafted phospholipid, a co-surfactant, and water.

20. The material as recited in claim 19 wherein the lipid is a phospholipid selected from the group consisting of dimyristolyphosphatidylcholine C-14, distearolyphosphatidylcholine C-18, or combinations thereof.

21. The material as recited in claim 19 wherein the material undergoes a phase change at a temperature selected from about 15° C. to 20° C.

22. The material as recited in claim 21 wherein the solid material defines lamellar spaces which are adapted to receive selected moieties.

23. The material as recited in claim 22 wherein the selected moieties are metal-containing moieties ranging in size from 2 nm to 20 nm.

* * * * *